(12) United States Patent
O'Hara

(10) Patent No.: US 11,413,317 B2
(45) Date of Patent: *Aug. 16, 2022

(54) **COMPOSITION COMPRISING *LACTOBACILLUS PLANTARUM* 2830 (ECGC 13110402)**

(71) Applicant: Probiotix Health Limited, Pontefract (GB)

(72) Inventor: Stephen Patrick O'Hara, Yorkshire (GB)

(73) Assignee: Probiotix Health Limited, Pontefract (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,994

(22) PCT Filed: Nov. 2, 2016

(86) PCT No.: PCT/GB2016/053390
§ 371 (c)(1),
(2) Date: Mar. 30, 2018

(87) PCT Pub. No.: WO2017/077286
PCT Pub. Date: May 11, 2017

(65) Prior Publication Data
US 2018/0289749 A1  Oct. 11, 2018

(30) Foreign Application Priority Data

Nov. 2, 2015 (GB) .................................. 1519327

(51) Int. Cl.
*A61K 35/74* (2015.01)
*A61P 9/12* (2006.01)

(52) U.S. Cl.
CPC ............... *A61K 35/74* (2013.01); *A61P 9/12* (2018.01)

(58) Field of Classification Search
CPC .................................. A61K 35/74; A61P 9/12

USPC ....................................................... 424/93.45
See application file for complete search history.

(56) References Cited

U.S. PATENT DOCUMENTS

2011/0177198 A1* 7/2011 Songisepp ........... A23C 9/1234
426/61

FOREIGN PATENT DOCUMENTS

| CN | 1844363 A | 10/2006 |
| CN | 102994420 A | 3/2013 |
| CN | 103598594 * | 2/2014 |
| KR | 20090113477 A | 11/2009 |
| KR | 20120125113 A | 11/2012 |
| KR | 20150074518 A | 7/2015 |
| WO | 2012149615 A2 | 11/2012 |
| WO | 2015067947 A1 | 5/2015 |
| WO | 2015067948 A1 | 5/2015 |
| WO | 0238165 A1 | 5/2022 |

OTHER PUBLICATIONS

Naruszewicz et al., Effect of *Lactobacillus plantarum* 299v on cardiovascular disease risk factors in smokers, American Journal of Clinical Nutrition, 76, (2002), p. 1249-1255.*

Arasu et al., In vitro importance of probiotic *Lactobacillus plantarum* related to medical field, Saudi Journal of Biological Science, 23, (2016) p. S6-S10.*

Chin Feng Liu, "Antihypertensive Effects of Lactobacillus-Fermented Milk Orally Administered to Spontaneously Hypertensive Rats" Journal of Agricultural and Food Chemistry, 2011, 59 (9), 4537-4543.

Khalesi, "Effect of Probiotics on Blood Pressure A Systematic Review and Meta-Analysis of Randomized, Controlled Trials", American Heart Association, Inc., Hypertension, Oct. 2014, 897-903.

* cited by examiner

*Primary Examiner* — Jennifer M. H. Tichy
(74) *Attorney, Agent, or Firm* — Sean Solberg

(57) ABSTRACT

The present invention relates to compositions comprising *Lactobacillus plantarum* 2830 (ECGC 13110402), or mutant strain or strains thereof, for use in the treatment or prevention of hypertension.

20 Claims, No Drawings

COMPOSITION COMPRISING *LACTOBACILLUS PLANTARUM* 2830 (ECGC 13110402)

TECHNICAL FIELD OF THE INVENTION

The invention relates to a composition comprising *Lactobacillus plantarum* 2830 (ECGC 13110402) which has been shown to be useful in the treatment, prevention and/or management of hypertension.

BACKGROUND TO THE INVENTION

Hypertension, otherwise known as high blood pressure, is a major health problem and is a risk factor for cardiovascular disease (CVD). The World Health Organisation (WHO) predicts that by the year 2020, up to 40% of all human deaths will be related to CVD. High cholesterol is often linked to hypertension due to a build up of cholesterol plaque in blood vessels.

Treatments for hypertension include angiotensin-converting enzyme (ACE) inhibitors, calcium channel blockers, diuretics and beta-blockers. However, all of these treatments are not without their side effects and therefore alternative or more natural treatments would be preferable.

The use of microbial strains in the reduction of cholesterol levels, and therefore potentially hypertension, by regulating bile acid regulators is known. Bile Salt Hydrolase (BSH) active probiotics have been shown to increase intraluminal bile acid deconjugation, resulting in increased levels of circulating deconjugated bile salts in humans and animal studies. As bile acids are deconjugated in the intestines, dietary and biliary cholesterol absorption is reduced and the recirculation of bile is altered, resulting in better control of low density lipoprotein cholesterol (LDL-C) levels in blood.

Studies have suggested a role of probiotics in reducing blood pressure. A meta-analysis of nine trials (Khalesi et. al., (2014), *Hypertension*, 64, (4), 897-903) showed probiotic consumption changed systolic BP by −3.56 mm Hg (95% confidence interval, −6.46 to −0.66) and diastolic BP by −2.38 mm Hg (95% confidence interval, −2.38 to −0.93) compared with control groups.

It is therefore an object of the present invention to provide an improved or alternative treatment for hypertension. It is also an object to provide a method of controlling or reducing blood pressure in an individual, and in particular, those having mild hypercholesterolaemia. It is a further object of the present invention to provide a probiotic composition which can be employed to reduce hypertension.

SUMMARY OF THE INVENTION

In an aspect of the present invention, there is provided a composition comprising *Lactobacillus plantarum* 2830 (ECGC 13110402), or mutant strain or strains thereof, for use in the treatment, control or prevention of hypertension.

In another aspect of the present invention, there is provided a composition comprising *Lactobacillus plantarum* 2830 (ECGC 13110402), or mutant strain or strains thereof, for use in the treatment, control or prevention of hypertension.

In a further aspect of the present invention, there is provided a composition comprising *Lactobacillus plantarum* 2830 (ECGC 13110402), or mutant strain or strains thereof, for use in the manufacture of a medicament for the treatment, control or prevention of hypertension.

It is preferred that the use of the composition in the treatment or prevention of hypertension is in an individual having at least mild hypercholesterolaemia.

In a yet further aspect of the present invention, there is provided a foodstuff or food supplement composition comprising *Lactobacillus plantarum* 2830 (ECGC 13110402), or mutant strain or strains thereof, for use in the reduction, prevention and/or control or hypertension.

In a yet further aspect of the present invention, there is provided a composition comprising *Lactobacillus plantarum* 2830 (ECGC 13110402), or mutant strain or strains thereof, for use in the manufacture of a food supplement or foodstuff for the treatment, control or prevention of hypertension.

In all aspects, the *Lactobacillus plantarum* 2830 (ECGC 13110402), or mutant strain or strains thereof, will preferably be present in the composition in an effective amount so as to reduce, prevent or control hypertension. Preferably, the *Lactobacillus plantarum* will be administered to an individual in an amount in the range of $10^5$ cfu/g to $10^{12}$ cfu/g. More preferably, will be administered in an amount in the range of $10^8$ cfu/g to $10^{10}$ cfu/g. The *Lactobacillus plantarum* may be administered to an individual in an amount in the range of $1\times10^5$ cfu to $1\times10^{12}$ cfu. More preferably, will be administered in an amount in the range of $1\times10^8$ cfu to $1\times10^{10}$ cfu. Most preferably, the *Lactobacillus plantarum* is in an amount of about 120 mg of the active strain providing about $1.8\times10^9$ cfu. Although it will be appreciated that different dosages may be administered depending upon the individuals' condition and degree of hypertension and other medical considerations.

Administration frequency would also be dependent upon an individuals' condition but preferably the composition would be administered twice daily.

The composition may be administered at any time of day, but preferably the composition is adminstered after meals. Administration after a meal advantageously accentuates the deconjugation effect of the BSH active *Lactobacillus plantarum*. Most bile acid secretion occurs after the consumption of a meal and the amount of bile acid secreted is proportionally related to the amount and type of food consumed.

It will be apparent to the skilled addressee that the composition may be in any easily administered form, for example in the form of a powder, tablet, or capsule. Alternatively, the composition may be in the form of a food stuff or food additive. The composition may be in the form of a drinkable liquid, a spread and/or powder which can be mixed with a solid or liquid food stuff. The composition could be used as a dietary supplement—for example to be blended with foods/drinks or consumed alongside foods/drinks.

The composition may further comprise an excipient or carrier compound to modify the release profile of one or more of the components through the intestinal environment. Release should occur at the most appropriate time in for reducing cholesterol absorption and thus control hypertension. Typically, the culture must survive relatively intact until it reaches the intestinal enterocytes of the small intestine.

The composition may be encapsulated. Many encapsulation techniques will be apparent to the skilled addressee and the one employed will be tailored to the required stability of the *Lactobacillus plantarum* during digestive transit. The encapsulate may comprise a prebiotic specifically tailored to the *Lactobacillus plantarum*.

The *Lactobacillus plantarum* may be concentrated and/or freeze dried. Advantageously *Lactobacillus plantarum* 2830

(ECGC 13110402) has demonstrated excellent freeze drying survival in pilot scale manufacturing trials.

The composition may further comprise one or more active ingredients selected from: vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B 1, riboflavoin or B25 niacin or B3, pyridoxine or B6, folic acid or B9, cyanocobalimin or B12, pantothenic acid, biotin), and combinations thereof.

Minerals may include, but are not limited to, sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to cartotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

The composition may further comprise one or more cholesterol reducing agents. For instance the composition may comprise beta glucans.

The composition may be administered with one or more statins, sterols and/or stanols. The composition may be co-administration with other hypertension active ingrements or used in as part of a combination therapy with such active ingredients to reduce the quantity of ingredients administered and therefore limit side effects.

Preferably the composition is stored at 4° C. or below. Bacterial growth is stabilised in this temperature range thus ensuring the stability of the composition.

The composition may further comprise a prebiotic growth medium which is specific to the growth of the *Lactobacillus plantarum* strain. The prebiotic growth medium will preferably be capable of being producing by the *Lactobacillus plantarum* strain by reverse enzyme reaction. The enzyme may comprise a saccharolytic or glycosidase enzymes. These saccharolytic or glycosidase enzymes may be derived from bacteria or fungi.

The prebiotic growth medium may comprise oligosaccharides such as galacto-oligosacharides, (GOS), gluco-oligosacharides, or fructo-oligosaccharides (FOS) in varying concentrations. It is preferred that the oligosaccharide form is substantially the same as the form produced by β-galactosidases, α-galactosidases, α- and β-glucosidases, α-mannosidases and β-xylosidases reverse reactions of the strain.

The prebiotic growth medium may be present in an amount which provides optimal growth and survival of the strain within the gut without impacting on safety, tolerance, and shelf life.

In accordance with a further aspect of the present invention, there is provided a method of treating an individual with or at risk of elevated hypertension by administering a composition having an effective amount of the *Lactobacillus plantarum*.

In accordance with a further aspect of the present invention, there is provided *Lactobacillus plantarum* 2830 (ECGC 13110402), or mutant strain or strains thereof, for use in a method of preventing, treating or modulating hypertension, wherein the *Lactobacillus plantarum* is administered in an amount in the range of $1\times10^5$ to $10^{12}$ cells twice a day.

More preferably, the *Lactobacillus plantarum* may be administered in an amount in the range of $1\times10^8$ to $1\times10^{10}$ cells. Most preferably, the *Lactobacillus plantarum* is administered in an amount about $1.8\times10^9$ cells. Also preferably, the *Lactobacillus plantarum* is administered in an amount of about 120 mg of the active strains.

The *Lactobacillus plantarum* may be administered shortly before, during or after morning and evening meals. Preferably, the *Lactobacillus plantarum* is administered shortly before breakfast and the evening meal.

The *Lactobacillus plantarum* may be administered as a medicine or as a dietary supplement.

The *Lactobacillus plantarum* may be in a freeze dried form.

The *Lactobacillus plantarum* may be administered with one or more additional hypertension active ingredient components. Such components may comprises: angiotensin-converting enzyme (ACE) inhibitors, calcium channel blockers, diuretics or beta-blockers. Furthermore, the *Lactobacillus plantarum* may be administered with one or more probiotics and/or prebiotics. The *Lactobacillus plantarum* may be administered in combination with a prebiotic growth medium which is specific to the growth of the *Lactobacillus plantarum* strain. The prebiotic growth medium will preferably be capable of being producing by the *Lactobacillus plantarum* strain by reverse enzyme reaction. The prebiotic growth medium may comprise oligosaccharides, which will preferably comprise galacto-oligosaccharide (GOS).

Preferably, the *Lactobacillus plantarum* is stored at 4° C. or below before administration.

In accordance with yet a further aspect of the present invention, there is provided a method of producing *Lactobacillus plantarum* 2830 (ECGC 13110402), or mutant strain or strains thereof, for use in the preparation of a medicament or food supplement, comprising:
a) fermenting *Lactobacillus plantarum* under conditions sufficient to produce a culture broth;
b) concentrating the *Lactobacillus plantarum* from the culture broth so as to form a concentrate of the *Lactobacillus plantarum* cells;
c) subjecting the concentrate to a cryoprotectant so as to form a mixture; and
d) freeze drying the mixture.

The survival rates for freeze drying the *Lactobacillus plantarum* cells by such a method is over 70%. Furthermore, the method has been advantageously found that the method produces the *Lactobacillus plantarum* cells in amounts of up to $8\times10^{11}$ cfu/g.

The method will of course be suitable for producing *Lactobacillus plantarum* 2830 (ECGC 13110402), or mutant strain or strains thereof, for a composition as herein above described, or indeed the *Lactobacillus plantarum* 2830 (ECGC 13110402) as herein above described.

It will be apparent to the skilled addressee that a number of the features of the composition listed in respect to the first aspect of the invention will be interchangeable with the composition administered in the present method.

DETAILED DESCRIPTION OF THE INVENTION

Embodiments of the present invention will now be described, by way of example only.

A human volunteer study was conducted to establish the safety, compliance and extent of hypertension control by administering compositions comprising *Lactobacillus plantarum* ECGC 13110402 to 49 mildly hypercholesterolaemic adults. The study was carried out independently by the Department of Food and Nutritional Sciences at the University of Reading, UK. The study was carried out according to the Helsinki declaration and written informed consent was obtained from all volunteers. The study protocol was approved by the Research Ethics committee of the University of Reading.

Subjects were male or female, aged 30-65 years. Subjects were excluded if they had had a previous cardiovascular event within the last 6 months, if secondary dyslipemias related to thyroid dysfunction were present, if they had used any drug affecting lipid metabolism in the previous 3 months, if they had a history of alcohol abuse, if they had taken antibiotics in the previous 6 months or if they had taken prebiotics/probiotic preparations in the last month.

Those who met the inclusion criteria were screened prior to the commencement of the study. A baseline blood sample was taken and their BMI and blood pressure were measured.

The study was a single-centre, prospective, randomized, double-blind, placebo-controlled, parallel-group trial. Subjects were randomly distributed into two groups: placebo or treatment with *Lactobacillus plantarum* ECGC 13110402. The placebo and treatment groups were provided with a blister packed DR 1 capsule. The treatment group received 120 mg of active *Lactobacillus plantarum* ECGC 13110402 providing a dose of $1.8 \times 10^9$ cells per capsule which was administered twice daily; once at breakfast and once in the evening. Participants were advised not to change their regular diet or physical activity throughout the trial period. Habitual diet was assessed by pre-validated 5-day food diaries (2 weekend and 3 week days).

Formulation details for the active and placebo formulations respectively are shown in tables 1 and 2 below:

TABLE 1

| Ingredient | mg/capsule | Billion for capsule | g for production |
|---|---|---|---|
| Probiotic powder | 120 | $8.4 \times 10^9$ | 567.00 |
| Corn starch | 118.6 | | 560.39 |
| Magnesium stearate | 3.2 | | 15.12 |
| Silicon dioxide | 3.2 | | 15.12 |
| Capsule DR size 1 white | 75 | | 354.38 |
| TOTAL | 320 | | 1512 |

TABLE 2

| Ingredient | mg/capsule | Billion for capsule | g for production |
|---|---|---|---|
| Corn starch | 238.6 | | 1127.39 |
| Magnesium stearate | 3.2 | | 15.12 |
| Silicon dioxide | 3.2 | | 15.12 |
| Capsule DR size 1 white | 75 | | 354.38 |
| TOTAL | 320 | | 1512 |

Volunteers were pre-screened 2 weeks prior to the study start and were advised to refrain from any pre/probiotic intake. The study consisted of two phases: a treatment period (12 weeks) and a wash-out period (4 weeks). The study included a baseline visit at selection, a visit at the midpoint and at the endpoint of the treatment period (weeks 0, 6 and 12, respectively), and a fourth visit after the wash-out period (week 16).

An initial set of analyses examined the demographic and outcome variables at baseline to ensure that the two groups were well matched. Continuous variables were analysed using the unpaired t-test, whilst the Chi-square test was used for the categorical variables.

Study outcomes between the two study groups were analysed in terms of changes between timepoints. Four study periods were examined for changes in outcomes: baseline to midpoint (0-6 weeks), midpoint to endpoint (6-12 weeks), baseline to endpoint (0-12 weeks) and endpoint to washout (12-16 weeks). Data for each analysis was restricted to the particular two timepoints in the analysis. The analyses were performed using analysis of covariance (ANCOVA). The latter timepoint was used as the outcome variable, with the earlier timepoint considered as a covariate. This approach is mathematically preferable to simply comparing the change over time between groups, as it takes into account the variable starting values for the test and control group.

There were no safety, compliance, or tolerance issues reported by volunteers throughout the study. Three volunteers dropped out of the study due to antibiotic treatment for non related illnesses which excluded them from further study participation.

The baseline characteristics (anthropometric measurements, systolic and diastolic pressure) were compared between the placebo (n=23) and active (n=23) groups and are shown in table 3 below. The results suggested no significant difference between the two study groups in terms of their demographics (age, sex) or for any of the anthropometric measures at baseline.

TABLE 3

| Variable | Placebo (n = 23) Mean (SD) | Active (n = 23) Mean (SD) | P-value |
|---|---|---|---|
| Age | 52.0 (8.4) | 52.3 (10.7) | 0.89 |
| Gender: Female | 14 (61%) | 18 (78%) | 0.20 |
| Gender: Male | 9 (39%) | 5 (22%) | |
| Weight | 79.2 (16.5) | 72.1 (12.0) | 0.10 |
| BMI | 26.8 (5.0) | 26.7 (3.7) | 0.96 |
| Waist | 92.3 (13.5) | 89.6 (12.0) | 0.49 |
| Systolic BP | 118.7 (16.0) | 119.2 (13.2) | 0.73 |
| Diastolic BP | 71.0 (12.2) | 73.0 (8.0) | 0.52 |

Changes in anthropometric measurements for all subjects (n=46) in the placebo and active treatment groups are shown from the baseline to the end of treatment after 12 weeks in table 4 below. The mean values and standard deviation for each measured outcome at baseline and after 12 weeks are shown in table 4. Group differences from the ANCOVA analyses are also shown with the mean difference and corresponding confidence interval. These are reported as outcome for active group minus outcome for placebo group adjusting for the baseline value. P-values indicating the significance of the results are reported. Body weight is expressed in kg, BMI in $kg/m^2$, waist circumference in cm and systolic/diastolic pressure in mmHg.

TABLE 4

| Outcome | Group | Baseline Mean (SD) | 12 weeks Mean (SD) | Change Mean (SD) [range] | % Change Mean (SD) [range] | Group Difference Mean (95% CI) | P-value |
|---|---|---|---|---|---|---|---|
| Weight | Placebo | 79.2 (16.5) | 79.3 (16.8) | 0.2 (1.7) [−2.6, 3.5] | 0.1 (2.1) [−3.3, 4.7] | 0 | 0.18 |
|  | Active | 72.1 (12.0) | 72.8 (12.6) | 0.7 (1.7) [−2.6, 3.8] | 0.9 (2.2) [−2.8, 4.9] | 0.7 (−0.3, 1.7) |  |
| BMI | Placebo | 26.8 (5.0) | 27.0 (5.2) | 0.3 (1.3) [−3.1, 4.2] | 0.9 (4.7) [−9.3, 15.5] | 0 | 0.41 |
|  | Active | 26.7 (3.7) | 27.2 (4.0) | 0.5 (0.9) [−1.1, 3.3] | 2.0 (3.3) [−3.9, 11.8] | 0.3 (−0.4, 1.0) |  |
| Waist | Placebo | 92.3 (13.5) | 90.5 (13.8) | −1.8 (6.4) [−14, 12] | −1.8 (6.8) [−17.3, 12.9] | 0 | 0.61 |
|  | Active | 89.6 (12.0) | 89.1 (11.0) | −0.5 (5.7) [−13, 13] | −0.2 (6.7) [−13.0, 16.3] | 0.9 (−2.6, 4.4) |  |
| Systolic pressure | Placebo | 117.7 (16.0) | 122.3 (11.4) | 4.7 (11.0) [−13, 28] | 4.9 (10.3) [−11.4, 31.1] | 0 | 0.15 |
|  | Active | 119.2 (13.2) 118.45 | 119.7 (13.0) | 0.5 (8.9) [−19, 21] | 0.7 (7.2) [−13.4 15.8] | −3.6 (−8.6, 1.4) −3% |  |
| Diastolic pressure | Placebo | 71.0 (12.2) | 73.5 (8.2) | 2.4 (9.0) [−15, 18] | 5.0 (13.6) [−14.4, 30.5] | 0 | 0.39 |
|  | Active | 73.0 (8.0) 72 | 73.0 (8.2) | 0.0 (5.9) [−9, 13] | 0.3 (8.4) [−10.5, 20.3] | −1.6 (−5.2, 2.1) −2.2% |  |

No significant changes were noted in the anthropometric parameters relevant to weight, BMI and waist circumference between baseline and end of treatment at 12 weeks.

There was group evidence of a difference in systolic and diastolic blood pressure between baseline and 12 weeks. The difference in systolic blood pressure was both statistically and clinically significant. In the all subject active treatment group systolic blood pressure was 3.6 mmHg lower (−3%) whilst diastolic pressure was reduced by 1.6 mmHg (2.2%). The majority of the reduction in systolic blood pressure occurred in the 6-12 week time period. This showed a statistically significant reduction (P=0.003) in systolic blood pressure of 6 mmHg (5.1%) in the active group when compared to the placebo group (data not shown in table 4). This is higher than the mean 3 mmHg pulse pressure reduction achieved by ACE inhibitors, ARBs and renin inhibitors and the 2 mmHg pulse pressure reduction with non-selective beta blockers. This reduction is also greater than the reduction of systolic BP by −3.56 mm Hg (95% confidence interval, −6.46 to −0.66) compared with control groups shown in a study analysing blood pressure reduction by probiotics (Khalesi et al, 2014).

The results show that *Lactobacillus plantarum* ECGC 13110402 has the potential to lower systolic blood pressure in at least mildly hypercholesterolaemic subjects.

Active *Lactobacillus plantarum* ECGC 13110402 and placebo capsules were stored at 4° C. throughout the study duration. Product stability was checked at baseline, 6 weeks and 12 weeks (end of treatment) of the study and no significant change was observed in bacterial numbers. No bacterial growth was detected in the placebo capsules.

Analysis of safety parameters did not show deleterious effects of consuming *Lactobacillus plantarum* (ECGC 13110402). *Lactobacillus plantarum* is a widely used probiotic which is considered Generally Regarded as Safe (GRAS) by the US Food and Drug Administration (FDA) and has a Qualified Presumption of Safety (QPS) designation by the European Food Standard Agency. This would suggest that *Lactobacillus plantarum* ECGC 13110402 has the potential to be a safe and effective treatment for the treatment of hypertension.

Industrial scale-up experiments were also conducted on *Lactobacillus plantarum* ECGC 13110402. The following activities were performed: a) testing of flasks for different hypoallergenic media; b) fermentations of 1-5 L, concentration and freeze drying of small amounts to study; c) testing of different cryoprotectants; d) testing of different freeze drying curves; e) fermentation in 80 L, concentration and freeze drying. The final step was a production in a 80 L fermenter which resulted in: (i) cell count>$8 \times 10^{11}$ cfu/g; (ii) Aw: 0.11; (iii) a quantity of 700 g of concentrated biomass, freeze dried and not diluted/standardized with any excipient. Therefore, this particular strain looked extremely promising from a manufacturing point of view. Survival rate of the cells was found to be at more than 70% and yields were at 1.25% which is extremely high.

The forgoing embodiments are not intended to limit the scope of the protection afforded by the claims, but rather to describe examples of how the invention may be put into practice.

The invention claimed is:

1. A composition comprising *Lactobacillus plantarum* 2830 deposited at the European Collection of Cell Cultures under Accession Number 13110402 for use in the treatment or prevention of hypertension, wherein the composition further comprises an oligosaccharide prebiotic growth medium which is specific to *Lactobacillus plantarum* 2830 and was produced by *Lactobacillus plantarum* 2830 by an enzyme reaction, wherein the enzyme is capable of catalyzing the reverse of the reaction which produced the oligosaccharide prebiotic growth medium, and wherein the *Lactobacillus plantarum* 2830 is freeze-dried.

2. The composition of claim 1, for use in the treatment or prevention of hypertension in an individual having hypercholesterolaemia.

3. The composition of claim 1, wherein the composition is incorporated into a foodstuff, food supplement, or drinkable liquid.

4. The composition of claim 1, wherein the *Lactobacillus plantarum* 2830 is administered in a dose in the range of $10^5$ cfu/g to $10^{12}$ cfu/g.

5. The composition of claim 1, wherein the composition is administered once or twice daily.

6. The composition of claim 1, wherein the composition is adminstered or taken after or during meals.

7. The composition of claim 1, wherein the composition further comprises one or more active ingredients selected from: vitamins, minerals, phytochemicals, antioxidants and combinations thereof.

8. The composition of claim 1, wherein the composition is administered or taken in combination with one or more of the following: statins, sterols and/or stanols.

9. The composition of claim 1, wherein the composition is stored at 4° C. or below.

10. The composition of claim 1, wherein the oligosaccharide prebiotic growth medium comprises galacto-oligosaccharide (GOS).

11. A method of treating an individual with, or at risk of, hypertension by administering the composition according to claim 1.

12. The method of claim 11, wherein the *Lactobacillus plantarum* 2830 is administered in an amount in the range of $10^5$ cfu/g to $10^{12}$ cfu/g.

13. The method of claim 11, wherein the composition is administered twice daily.

14. The method of claim 11, wherein the composition is adminstered after meals.

15. The method of claim 11, wherein the *Lactobacillus plantarum* 2830 is further concentrated.

16. The method of claim 11, wherein the composition further comprises one or more active ingredients selected from: vitamins, minerals, phytochemicals, antioxidants and combinations thereof.

17. The method of claim 11, wherein the composition further comprises one or more cholesterol reducing agents.

18. The method of claim 11, wherein the composition is administered in combination with one or more of the following: statins, sterols and/or stanols.

19. The method of claim 11, wherein the composition is stored at 4° C. or below.

20. The composition of claim 1, wherein the *Lactobacillus plantarum* 2830 is further concentrated.

* * * * *